United States Patent
Vogt

(10) Patent No.: US 9,072,834 B2
(45) Date of Patent: Jul. 7, 2015

(54) METHOD FOR RELEASE OF ACTIVE SUBSTANCES AND ACTIVE SUBSTANCE RELEASE SYSTEMS

(71) Applicant: Heraeus Medical GmbH, Wehrheim (DE)

(72) Inventor: Sebastian Vogt, Erfurt (DE)

(73) Assignee: Heraeus Medical GmbH, Wehrheim (DE)

( * ) Notice: Subject to any disclaimer, the term of this patent is extended or adjusted under 35 U.S.C. 154(b) by 0 days.

(21) Appl. No.: 14/065,738

(22) Filed: Oct. 29, 2013

(65) Prior Publication Data

US 2014/0128833 A1    May 8, 2014

(30) Foreign Application Priority Data

Nov. 7, 2012 (DE) .......................... 10 2012 021 675
Dec. 21, 2012 (DE) .......................... 10 2012 025 143

(51) Int. Cl.
*A61M 37/00* (2006.01)
*A61M 5/20* (2006.01)
(Continued)

(52) U.S. Cl.
CPC ............ *A61M 5/2046* (2013.01); *A61K 9/0009* (2013.01); *A61K 9/0024* (2013.01); *A61L 27/50* (2013.01); *A61L 27/54* (2013.01); *A61L 2300/406* (2013.01); *A61L 2300/602* (2013.01)

(58) Field of Classification Search
CPC .................. A61M 5/2046; A61M 2025/0056; A61F 2002/30677; A61F 2002/30062; A61B 17/56
USPC .......................................... 604/144, 145, 500
See application file for complete search history.

(56) References Cited

U.S. PATENT DOCUMENTS 5,496,557 A * 3/1996 Feijen et al. .................. 424/426
5,951,538 A   9/1999 Joshi et al.
(Continued)

FOREIGN PATENT DOCUMENTS

DE   102009007195 A1   8/2010
JP   S63260574          10/1988
(Continued)

OTHER PUBLICATIONS

German Office Action for corresponding German Application No. DE 10 2012 025 143.2 dated Jun. 14, 2013.
(Continued)

*Primary Examiner* — Nicholas Lucchesi
*Assistant Examiner* — Gerald Landry, II
(74) *Attorney, Agent, or Firm* — Norris McLaughlin & Marcus, P.A.

(57) ABSTRACT

A device releases a fluid active substance, the device has at least one hollow space containing the fluid active substance, whereby the device contains water and a reducing agent, which are or can be made to be in communication such that a chemical reaction of the water and the reducing agent produces a gas and the gas effectively communicates with the fluid active substance such that the gas pressure thus generated presses the fluid active substance out of at least one opening of the hollow space out of the device. A medical implant incorporates the device, and a method releases a fluid active substance from a hollow space of the medical implant, in which a gas is produced through a chemical reaction of liquid water and a reducing agent, and the resulting gas pressure is used to expel the fluid active substance out of at least one opening of the hollow space.

19 Claims, 3 Drawing Sheets

Figure 1:
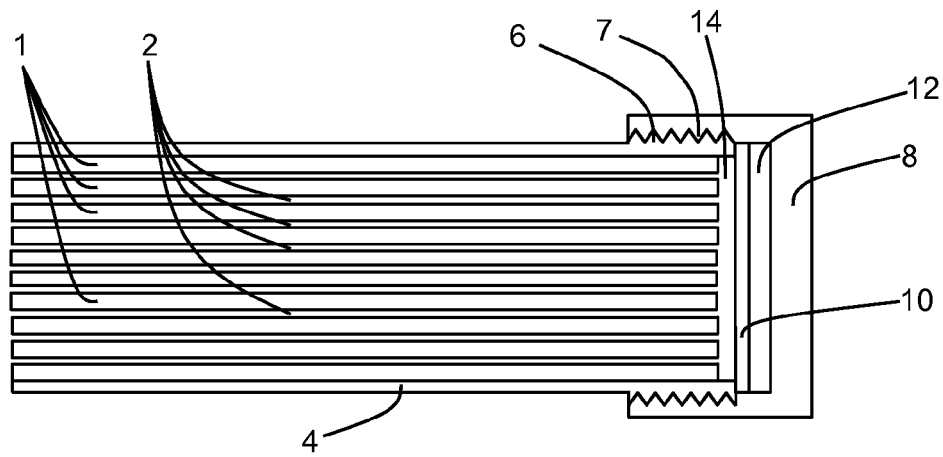

(51) Int. Cl.
  *A61K 9/00*     (2006.01)
  *A61L 27/50*    (2006.01)
  *A61L 27/54*    (2006.01)

(56) References Cited

U.S. PATENT DOCUMENTS

| | | | |
|---|---|---|---|
| 7,077,859 B2 * | 7/2006 | Sirhan et al. | 623/1.15 |
| 7,255,713 B2 | 8/2007 | Malek | |
| 7,300,439 B2 | 11/2007 | May | |
| 7,794,484 B2 | 9/2010 | Stone et al. | |
| 8,619,256 B1 * | 12/2013 | Pelletier et al. | 356/335 |
| 2004/0186576 A1 * | 9/2004 | Biscup et al. | 623/17.12 |
| 2006/0253060 A1 * | 11/2006 | Alimi | 604/19 |
| 2008/0086113 A1 * | 4/2008 | Tenney et al. | 604/892.1 |
| 2008/0215138 A1 * | 9/2008 | Bates et al. | 623/1.42 |
| 2008/0249638 A1 * | 10/2008 | Asgari | 623/23.75 |
| 2010/0042214 A1 | 2/2010 | Nebosky et al. | |
| 2010/0145301 A1 * | 6/2010 | Magal | 604/503 |
| 2010/0217401 A1 | 8/2010 | de Beaubien | |
| 2011/0015754 A1 | 1/2011 | Leonard et al. | |
| 2011/0202032 A1 * | 8/2011 | Shih et al. | 604/500 |
| 2012/0029470 A1 * | 2/2012 | Juan et al. | 604/506 |
| 2012/0041565 A1 | 2/2012 | Kraus | |
| 2013/0060188 A1 * | 3/2013 | Bedwell et al. | 604/21 |
| 2014/0031769 A1 * | 1/2014 | de Juan et al. | 604/294 |

FOREIGN PATENT DOCUMENTS

| | | |
|---|---|---|
| JP | 2001513366 A | 9/2001 |
| JP | 2010216445 A | 9/2010 |
| JP | 2012500056 A | 1/2012 |
| WO | 97/13007 A1 | 4/1997 |
| WO | 2007/106557 A2 | 9/2007 |

OTHER PUBLICATIONS

Li, Po-Ying, et al., "An Electrochemical Intraocular Drug Delivery Device", Sensors and Actuators, Jun. 26, 2007, pp. 41-48, A 143, Elsevier B.V., California, United States of America.

European Search Report for corresponding EP Application No. 13189543.5 dated May 9, 2014.

Japanese Office Action for corresponding JP Application No. 2013-225328 dated Nov. 4, 2014.

* cited by examiner

METHOD FOR RELEASE OF ACTIVE SUBSTANCES AND ACTIVE SUBSTANCE RELEASE SYSTEMS

The invention relates to a device for release of an active substance as well as a method for release of an active substance and a medical implant comprising said device.

The device and the method are designed for active continuous release of active substances, in particular for local release of antibiotic agents. The active substance release systems can be used in the form of spacers, as active component of spacers and also as implant. As a matter of principle, said methods and devices are not designed to be ingested, but rather are implemented by means of devices with containers for the active substance that are implanted into the body. More specifically, the invention relates to so-called spacers that are used as intermediate replacement for endoprostheses in the body in order to fight infection of the surrounding tissue.

Cemented and non-cemented total articular endoprostheses (TEPs) are currently the state of the art in orthopaedics. Unfortunately, TEPs are associated with a small number of early and late infections. Infected TEPs usually necessitate a revision surgery. Said revision surgeries can be subdivided into one-stage and two-stage operations. Two-stage revision surgery involves removing the infected TEP first, followed by debridement of the infected bone and soft tissue, and subsequently inserting a spacer as temporary placeholder. In this context, it is customary to use industrially pre-made spacers that may contain an antibiotic or to use tailor-made spacers made of PMMA bone cement which are either shaped freely or through the use of casting moulds by the surgeon. Said spacers can be fabricated in patient-specific manner through tailor-made doping of the PMMA bone cement used in them with antibiotics in accordance with the antibiotic profile of the pathogens underlying the infection.

Spacers usually stay in place in the patient for a period of several weeks, often for 6 to 8 weeks, until the infection subsides. Subsequently, the spacer is removed in a second surgery, the surrounding tissue is again subjected to debridement, and then the revision prosthesis of a cemented or non-cemented type is inserted.

Aside from industrially pre-made PMMA spacers and tailor-made PMMA spacers, which may contain one or more antibiotic(s), spacers which, as such, do not contain antibiotics have been proposed as well. Said spacers contain cavities that can be filled with antibiotic solutions by the medical user.

US 2010/042214 A1 discloses spacers that contain at least one hollow space which communicates with the outside of the spacers by means of channels. The active substance solution can be introduced into the hollow space and then exits through the channel openings on the outside of the spacers.

A similar spacer containing at least two tanks for accommodation of active substance solutions was described in US 2011/015754 A1. Said tanks possess openings through which the active substance solutions can be dispensed into the surroundings.

US 2010/217401 A1 proposed porous screws possessing on their inside an active substance reservoir communicating with the pores. Further very similar devices are already known from specifications U.S. Pat. No. 7,794,484 B2, U.S. Pat. No. 7,255,713 B2, and U.S. Pat. No. 7,300,439 B2.

In said fillable spacers and other active substance carriers into which active substance solutions can be filled, the active substances are present in liquid, dissolved form and exit through simple diffusion.

This is disadvantageous in that it may lead to variations in the release of active substances, in that the active substance release is terminated prematurely, and in that there may be an asymptotic decrease in the release of the active substances.

Accordingly, it is the object of the invention to overcome the disadvantages of the prior art. Specifically, the invention is to provide a device and a method, in which active substances can be released continuously and, if possible, evenly over a period of up to several weeks.

The objects of the invention are met by a device for releasing a fluid active substance, comprising at least one hollow space containing the fluid active substance, whereby the device contains water and a reducing agent, which are or can be made to be in communication such that a chemical reaction of the water and the reducing agent produces a gas in the device and the gas effectively communicates with the fluid active substance such that the gas pressure thus generated presses the fluid active substance out of at least one opening of the hollow space out of the device.

In this context, it is preferred that the gas thus generated is hydrogen.

According to a development, the invention can provide that the water for the chemical reaction is part of a liquid aqueous solution that forms the fluid active substance, whereby the fluid active substance preferably is an aqueous solution comprising at least one pharmaceutically active substance, particularly preferably an aqueous solution comprising at least one antibiotic.

This renders the design particularly easy and inexpensive to implement since the fluid active substance concurrently provides the propellant (the gas) for expelling the fluid active substance from the device.

Moreover, the invention can provide the reducing agent to be a metallic surface, whereby the metallic surface preferably has a negative standard potential, whereby the metallic surface particularly preferably contains or consists of magnesium, iron or alloys comprising magnesium and/or iron.

Said surfaces corrode slowly such that an even and long-lasting release of the active substance can be ensured through said design.

In this context, the invention can provide the reducing agent to be magnesium and a noble metal forming an electrochemical cell or the reducing agent to be a mixture of a quickly corroding metal and a slowly corroding metal.

This variant allows the release of gas to be adjusted particularly well and accurately, including over long periods of time.

A particularly preferred development of the invention can provide that at least a sufficient mass of reducing agent and/or water to produce an amount of gas that takes up at least 30% of the hollow space volume, preferably at least 50% of the hollow space volume, particularly preferably at least 80% of the hollow space volume, is arranged in the device.

Said quantities ensure that a sufficient part of the active substance is expelled from the device. Particularly preferably, the invention provides that a sufficient mass of reducing agent to produce an amount of gas that corresponds to 70% to 90% of the hollow space volume is arranged in the device. Under these conditions, exactly the correct amount of reducing agent is present such that no unnecessary excess of gas is produced and would have to be re-absorbed by the body, even if the device remains indwelling in the body for an extended period of time.

Another particularly preferred variant of the invention can provide that the at least one hollow space is formed, at least over regions thereof, by one or more capillary-shaped tubes in the device that extend on one side to an opening in the surface of the device, whereby the hollow spaces preferably are formed by a plurality of tubes that are parallel and capillary-shaped, at least over regions thereof.

Said design is very simple and very safe. The capillary-shaped tubes ensure that the surface tension of an aqueous solution contained therein provides for the aqueous solution to be expelled from the capillary-shaped tubes first, since the gas cannot be pressed through the capillaries past the aqueous solution. Moreover, the invention particularly preferably provides the capillary-shaped tubes to be capillaries. The capillaries preferably have a diameter of less than 500 µm, particularly preferably of less than 200 µm.

In this context, the invention can provide the reducing agent to be arranged on the end of the capillary-shaped tube or capillary-shaped tubes that is opposite from the corresponding opening, whereby the reducing agent is arranged in the hollow space and is connected to the surface of the device solely through the opening of the tube, whereby the fluid active substance preferably contacts the reducing agent as an aqueous solution.

The gas is thus produced on the desired side of the capillary-shaped tubes. Moreover, the capillary-shaped tubes can preferably be coated by the reducing agent on the side of the tubes facing away from the opening towards the outside.

According to an alternative, particularly preferred embodiment, the invention can provide a plunger to be arranged in the hollow space that can be shifted towards the at least one opening of the hollow space, and the plunger to subdivide the hollow space into a first part comprising the at least one opening and a second part that is or can be closed, whereby the fluid active substance is arranged in the first part and the reducing agent and water are arranged in the second part such that the gas pressure generated in the closed second part of the hollow space drives the plunger towards the at least one opening and thus presses the fluid active substance out of the first part of the hollow space through the at least one opening out of the device.

Said design allows even a more substantial amount of the active substance to be released slowly in the same space as would be possible upon the use of capillaries, since the hollow space, as a usable space, is significantly larger relative to the external dimensions of the device.

In this context, the invention can provide an overflow channel to be arranged in the internal wall of the hollow space, which, in a starting position of the plunger, connects the first part and the second part of the hollow space, and the second part of the hollow space to comprise a closure opening, which can be or is closed by means of a closure such that both parts of the hollow space can be filled through the closure opening with the same aqueous solution, which forms the active substance and provides the liquid water for the chemical reaction, whereby the closure is designed such that it pushes the plunger in the hollow space towards the at least one opening past the overflow channel upon the closure opening being closed such that the over-flow channel no longer connects the first part and the second part of the hollow space when the closure is fully inserted and the plunger separates the first and the second part of the hollow space from each other in a gas-tight manner.

Said design allows the fluid active substance to also be used as source of the gas.

The invention can, in turn, provide at least one fin and/or at least one hollow cylinder to be arranged on the closure and to extend into the first part of the hollow space when the closure is inserted and to push the plunger towards the at least one opening past the overflow channel upon closing.

This allows the two hollow space parts to be separable from each other easily and automatically upon the second hollow space being closed.

According to a development, the invention can provide a thread, preferably an external thread, to be arranged on the closure, and the hollow space to comprise a counter-thread, preferably an internal thread, on the closure opening, such that the closure pushes the plunger towards the at least one opening past the overflow channel when the closure is being screwed in.

This enables controlled propulsion of the plunger through the closure (or the closure cap and/or screw cap, as the case may be). Moreover, the thread can serve a sealing function.

Moreover, the invention can provide at least one valve element for gas discharge in the presence of an overpressure to be arranged on the second part of the hollow space, preferably a burst disc or an overpressure valve to be arranged on the second part of the hollow space, whereby the valve element preferably is arranged in the plunger such that an opening towards the second part of the hollow space is produced in the plunger in the presence of a sufficient overpressure.

This increases the safety of the device since any undesired overpressure can be prevented.

Devices according to the invention can also be characterised in that the at least one hollow space, in particular the capillary-shaped tubes, consist(s) of synthetic polymers and/or partially-synthetic polymers.

Said materials can be used particularly well and are particularly well-suited for devices according to the invention.

According to a preferred development, the invention can provide the at least one opening to be closed by means of a perforated body, preferably by means of a perforated rubber body, whereby the perforated body is arranged in the region of the at least one opening.

This allows premature inadvertent leakage of the fluid active substance from the device to be prevented.

The objects of the invention are also met by a medical implant comprising said device, whereby the medical implant preferably is a hip spacer or a knee spacer.

The objects of the invention are also met by a method for releasing a fluid active substance from a hollow space of a medical implant, in which a gas is produced through a chemical reaction of liquid water and a reducing agent, and the resulting gas pressure is used to expel the fluid active substance out of at least one opening of the hollow space.

The method according to the invention is preferably implemented using a device according to the invention.

The method can provide hydrogen to be produced as the gas.

The use of hydrogen as the gas is advantageous in that the water of the aqueous solutions can be used as source of the gas and thus no additional gas sources are required.

The invention also proposes to use a metallic surface as the reducing agent, preferably a metallic surface having a negative standard potential to be used, particularly preferably magnesium, iron or alloys comprising magnesium and/or iron to be used as metallic surface, whereby the gas, in particular the hydrogen, is produced through corrosion of the metallic surface.

Said surfaces corrode slowly such that an even and long-lasting release of the active substance can be ensured through said design.

In this context, the invention can provide magnesium and a noble metal to be used as reducing agent and the gas to be produced through an electrochemical reaction.

Said metals are corroded by water sufficiently strongly, but also sufficiently slowly, to ensure long-lasting release of the fluid active substance. Moreover, said metals are non-objectionable from a medical point of view in terms of their use in the human body.

Alternatively, the invention can provide a mixture of a quickly corroding metal and a slowly corroding metal to be used as the reducing agent.

This allows the corrosion and thus the flow rate of the fluid active substance to be adjusted even more accurately.

And lastly, the method according to the invention proposes the liquid water used for the chemical reaction to be part of an aqueous solution that forms the fluid active substance, whereby it is preferred to use an aqueous, pharmaceutically active solution as fluid active substance, particularly preferably an aqueous solution comprising at least one antibiotic.

The scope of the invention also includes a method for active substance release that is characterised in that an aqueous active substance solution is expelled from a hollow space by means of hydrogen that is produced through corrosion of at least one metal or metal alloy upon contact with an aqueous electrolyte solution, whereby the at least one metal or the at least one metal alloy is arranged in at least one part of the hollow space.

The invention is based on the surprising finding that the method according to the invention and the device according to the invention can be used successfully to release active substances continuously over a period of several weeks by means of an active transport mechanism, whereby said transport mechanism is active at body temperature without requiring an external or internal energy source for this purpose. The invention is based on the surprising finding that magnesium, magnesium alloys, iron, and iron alloys corrode when exposed to electrolyte solutions and body fluids, such as blood, whereby hydrogen is released as a side product and the products of said chemical reaction (i.e. the hydrogen gas) can be used as propellant for dispensing an active substance from a hollow space. The corrosion rate is a function of the metal used or of the metal alloy used, of the surface-volume ratio of the metal or metal alloy, and is up to a period of several weeks if the design is appropriate. This means that hydrogen is released continuously during the corrosion process and is used to expel the active substance from the hollow space. The corrosion of magnesium produces magnesium hydroxide, which is non-toxic and absolutely non-objectionable. Magnesium is a natural constituent of the human body. Iron corrodes to form iron oxides. These are also considered to be medically non-objectionable. Iron is a natural constituent of the human body and is vital to man. Therefore, said two metals are particularly preferred for use in a device according to the invention and in a method according to the invention.

The underlying rationale of the invention is based on using the hydrogen, which is necessarily released during the corrosion of metals, to drive the continuous release of pharmaceutical active substance solutions. A plethora of water-soluble active substances are present in the form of the salt and form electrolyte solutions when dissolved in water. Pertinent examples include the antibiotics, gentamicin sulfate, tobramycin sulfate, clindamycin hydrochloride, and vancomycin hydrochloride. Referring to active substances that are soluble or at least suspended in water and are not present in the form of a salt, the active substance can also be dissolved or suspended in conventional medical electrolyte solutions such as physiological saline or Ringer solutions.

The scope of the invention includes an implementation variant of the device that is a device for releasing active substances, characterised in that a) at least one capillary-shaped hollow space possessing at least one opening, is arranged in the device;

b) whereby the hollow space is filled, at least partly, with aqueous active substance solution;

c) whereby the aqueous active substance solution contacts a metal or a metal alloy at least at one site;

d) whereby the metal or the metal alloy is enclosed through a gas-tight shell; and e) whereby the metal or the metal alloy is connected in liquid-tight and gas-tight manner to the at least one capillary-shaped hollow space through at least one opening in the shell such that the hydrogen produced through corrosion of the metal or metal alloy and the aqueous active substance solution can exit only through the at least one capillary-shaped hollow space.

This means that the fluid active substance, which can be an aqueous active substance solution or an active substance suspension, is first introduced into the capillary-shaped hollow space, for example through aspiration. The active substance solution contacts the metal or metal alloy. The corrosion process commences and hydrogen is released continuously during this process. This expels the active substance solution or active substance suspension continuously from the capillary-shaped hollow space.

An advantageous refinement of the invention consists of at least a sufficient mass of metal or metal alloy to release a volume of hydrogen due to corrosion of the metal or metal alloy that takes up at least 50% by volume of the capillary-shaped hollow space being arranged in the device.

Even minute amounts of metal are sufficient to release sufficient volumes of hydrogen. Accordingly, 1 mg magnesium releases approx. 0.9 ml hydrogen under standard conditions. For continuous active substance release, hydrogen volumes of just a few millilitres are absolutely sufficient. Therefore, milligram quantities of metal are sufficient to drive a release system according to the invention.

The scope of the invention also includes at least two capillary-shaped hollow spaces being present, whereby bundles of capillaries are particularly preferred. The bundles of capillaries or bundles of capillary-shaped tubes can advantageously be arranged in tube-shaped containers or containers of arbitrary shape, whereby at least one end of the bundles of capillaries needs to open to liquids and gases. It is particularly advantageous for the bundles of capillaries to be cast together with a plastic material in the container in gas-tight manner. The containers can be closed on one side through caps with screw thread or caps lockable by means of snap-in means, whereby the metal or metal alloy is situated on the inside of the screw cap. It is feasible just as well to combine two containers of bundles of capillaries, whereby both containers are coupled to each other at one end each in gas-tight manner, whereby the metal/metal alloy is arranged at the transition between the two bundles of capillaries. The scope of the invention can also provide that the inside of the capillary-shaped hollow spaces is coated with the metal or metal alloy as reducing agent.

Moreover, the invention can provide the capillaries to consist of synthetic polymers and/or partially synthetic polymers.

The scope of the invention also includes a device for releasing active substances, characterised in that a) a hollow body is arranged in the device, whereby the hollow body comprises at least one opening;

b) at least one overflow channel is arranged in a distal part of the hollow body on the inside of the hollow space;

c) a plunger that can be shifted in axial direction of the hollow body is arranged in the hollow space;

d) a closure is arranged on the distal end of the hollow body and is provided as a pestle on its proximal side and can be moved towards the proximal end of the hollow space through rotation or shifting;
e) whereby the plunger initially is arranged such that the proximal hollow space communicates in liquid-permeable manner with the distal hollow space that is situated between the plunger and the closure; and
f) whereby at least one body made of metal or a metal alloy is situated in the distal hollow space and corrodes while releasing hydrogen when it contacts aqueous solution.

According to the invention, it is preferred to use an aqueous electrolyte solution as aqueous solution.

Said device works such that the fully assembled device, in which the plunger is arranged between two openings or ends of an overflow channel, as the case may be, is first filled with the aqueous active substance solution or active substance suspension, as the case may be, by means of the at least one opening (closure opening) of the device. The two openings of the overflow channel connect the proximal hollow space to the distal hollow space. The overflow channel can be provided as a simple axial groove. In this context, the aqueous active substance solution or the aqueous active substance suspension, as the case may be, flows from the proximal hollow space through the overflow channel past the plunger into the distal hollow space. The metal or metal alloy is situated in the distal hollow space. The active substance solution or active substance suspension, as the case may be, contacts the metal or metal alloy. Then, the user moves the closure towards the proximal end of the device by rotating or shifting it. The proximal end of the closure is provided as a pestle. Said pestle moves the plunger in proximal direction. In the process, the plunger travels over the proximal opening of the overflow channel. The distal hollow space is thus closed off from the proximal hollow space in gas-tight manner. At least a small portion of the active substance solution or active substance suspension, as the case may be, and the metal or metal alloy are situated in the gas-tight distal hollow space. This starts the corrosion process. Hydrogen is then produced continuously in the distal hollow space and moves the plunger towards the proximal end of the device and thus continuously presses the active substance solution or active substance suspension, as the case may be, situated in the proximal hollow space out of the at least one opening (proximal opening).

An advantageous variant of an embodiment consists of at least one opening element for gas discharge in the presence of an overpressure to be arranged in the device, whereby a burst disc or an overpressure valve is preferred, which are preferably arranged in the plunger in appropriate manner such that a connection of the distal hollow space to the proximal hollow space is established in the presence of an overpressure.

Moreover, the invention can advantageously provide the proximal hollow space to possess two openings arranged axially behind each other, whereby the axial distance of the two openings is larger than the height of the plunger. This allows the plunger to travel over the first opening at the end of the press-out motion, whereby the remaining active substance solution or active substance suspension, as the case may be, is pressed out through the second opening. Once the plunger has travelled over the first opening, the hydrogen can escape and an overpressure can be safely prevented from becoming established in the device.

Moreover, the invention can provide that at least a sufficient mass of metal and/or metal alloy to release a volume of hydrogen by corrosion of the metal or metal alloy that takes up at least 30% by volume of the proximal hollow space, preferably at least 50% by volume of the proximal hollow space, particularly preferably at least 80% of the proximal hollow space, at room temperature is arranged in the device. The proximal hollow space corresponds to the second part of the hollow space.

The two active substance release systems according to the invention can be used as such as hip spacer, as knee spacer, as local antibiotic support, and as a component of hip spacers, knee spacers, and local antibiotic supports.

Aside from this, all other active substances that can be dissolved or suspended in water can be released using the active substance release systems according to the invention, which can take any shape.

Figure 2:
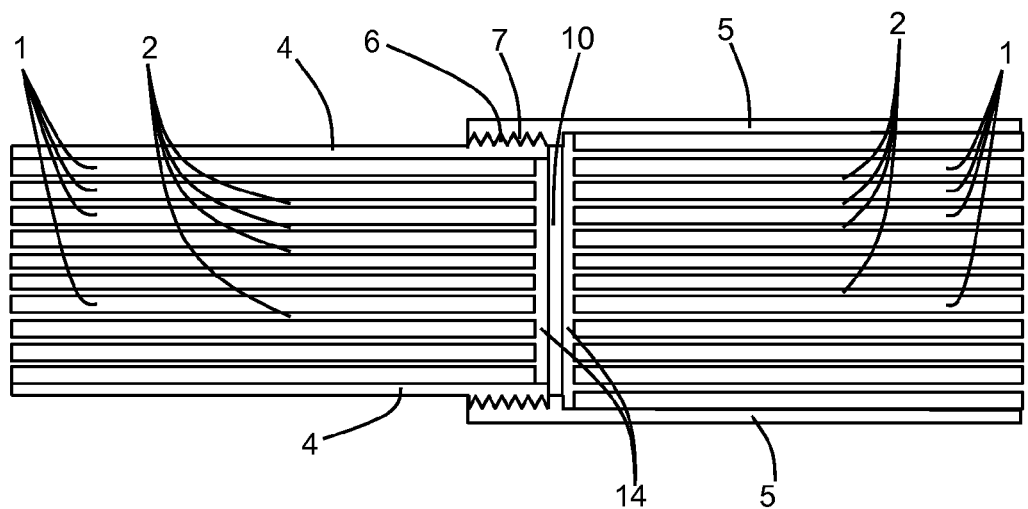
Figure 3:
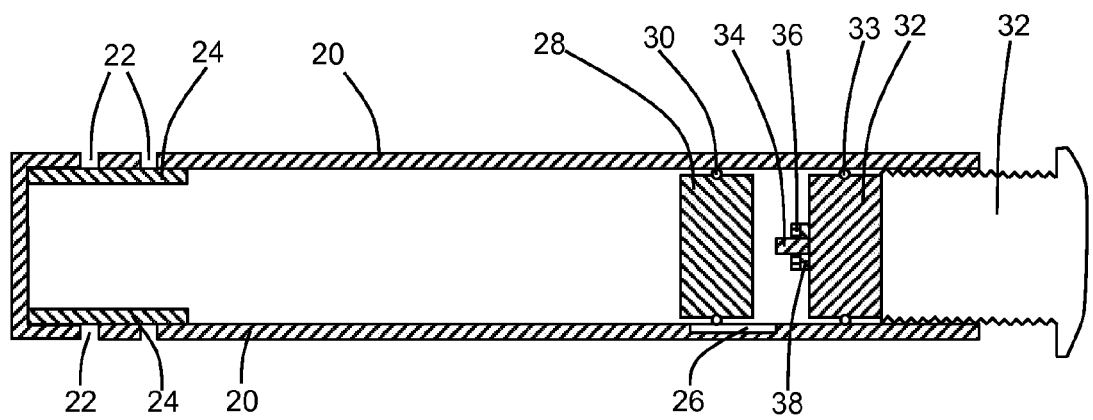
Figure 4:
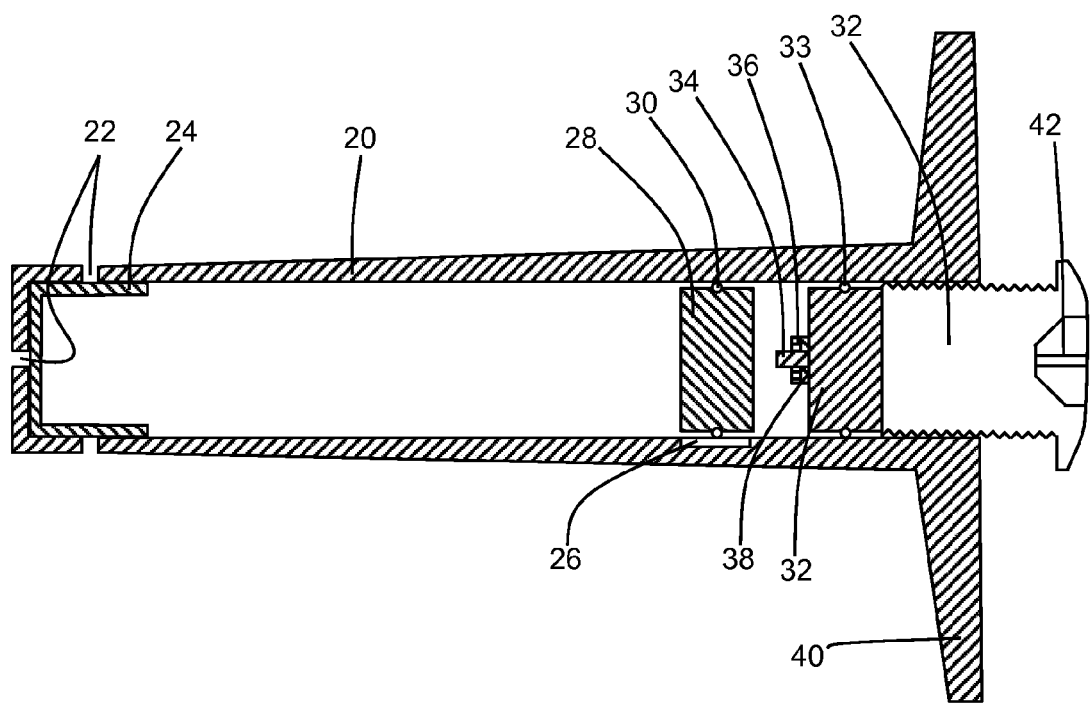
Figure 5:
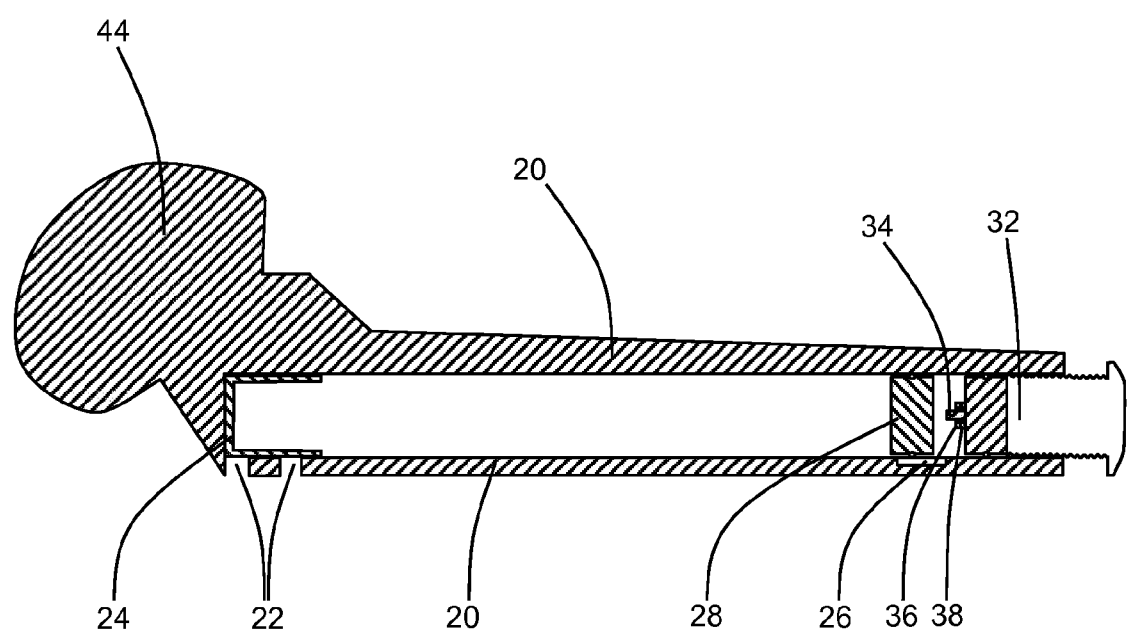

Exemplary embodiments of the invention shall be illustrated in the following on the basis of five schematic figures, though without limiting the scope of the invention. In the figures:

FIG. 1: shows a schematic cross-sectional view of a device according to the invention;

FIG. 2: shows a schematic cross-sectional view of an alternative device according to the invention;

FIG. 3: shows a schematic cross-sectional view of yet another device according to the invention;

FIG. 4: shows a schematic cross-sectional view of a medical implant according to the invention; and FIG. 5: shows a schematic cross-sectional view of a spacer according to the invention.

FIG. 1 shows a schematic cross-sectional view of a device according to the invention. The device includes a base body 1 made of a polymer that comprises a plurality of capillaries 2. The capillaries 2 can be made of a synthetic or a partially-synthetic polymer which are either cast into the base body 1 or are fabricated from the same material as the base body 1 and were made in or jointly with the base body 1. The base body 1 is arranged in a housing 4 made of a biocompatible material.

An external thread 6 is provided on one end of the housing 4 and has an internal thread 7 of a cap 8 screwed onto it. The cap 8 also consists of a biocompatible material. A metal plate 10 made of magnesium and/or iron is arranged in the lid of the cap 8 and is connected to the lid of the cap 8 by means of an elastic connector 12. The threads 6, 7 are designed such that the limit stop for the cap 8 being fully screwed onto the housing 4 is selected appropriately such that an internal space 14 is formed between the base body 1 and the cap 8. Instead of having an elastic connector 12, the internal space 14 can just as well extend further in this place such that the metal plate 10 is largely surrounded by the internal space 14 and/or the content thereof, as the case may be. The internal space 14 and the capillaries 2 form a hollow space 2, 14 in the device. Said hollow space 2, 14 in the device, i.e. the capillaries 2 and the internal space 14, contains an aqueous antibiotics solution.

FIG. 2 shows a schematic cross-sectional view of a similar design. The design comprises two base bodies 1 having capillaries 2, which are arranged in a first housing 4 and in a second housing 5. The first housing 4 comprises an external thread 6 and the second housing 5 comprises an internal thread 7, and the two housings 4, 5 are screwed to each other. A metal plate 10 made of magnesium and/or iron or an alloy thereof is arranged between the two housings 4, 5 and can be part of either of the two housings 4, 5 or can be a separate metal plate 10 to be arranged between the housings 4, 5 before these are screwed together. Internal spaces 14 are formed in each housing 4, 5 between the base bodies 1 and the metal plate 10. Preferably, the metal plate 10 closes tightly against the walls of at least one of the housings 4, 5 such that the internal spaces 14 are separated from each other. However, it is feasible just as well that the internal spaces 14 are connected to each other by means of the metal plate 10 or through channels on or in the housings 4, 5. Then, the same gas pressure becomes established in each internal space 14 (see the explanation in the subsequent description in this context).

The capillaries 2 and the internal spaces 14 form hollow spaces 2, 14 in the device that are filled with an aqueous solution of at least one pharmaceutically active substance. The same method according to the invention is then implemented in either of the two exemplary embodiments according to FIGS. 1 and 2:

The water in the aqueous antibiotics solution or the aqueous solution of the pharmaceutically active substance undergoes a chemical reaction with the magnesium and/or iron at the metal surface of the metal plate, whereby the metal or metals corrode, which produces metal oxides and gaseous hydrogen. The hydrogen gas thus produced has a significantly larger volume at standard conditions such that it expands in the internal space 14 and thus presses the aqueous solution out of the capillaries 2 and out of the device. The chemical reaction of corrosion of the metal plate 10 proceeds sufficiently slowly in this context such that the aqueous solution is pressed out of the capillaries 2 only slowly and the device therefore releases the active sub-stances evenly over a long period of time. The duration and rate of hydrogen evolution and thus of the active substance release of the device can be adjusted through appropriate selection of the reducing agent, i.e. the selection of the metals of the alloy and the surface properties thereof.

Further modifications within the scope of the invention are discussed in the following based on FIGS. 1 and 2. The bundles of capillaries 2, or the bundles of capillary-shaped tubes 2 as the case may be, are arranged, for example, in tube-shaped containers 4, 5, whereby at least one end of the bundles of capillaries 2 is open to liquids and gases. It is particularly expedient for the bundles of capillaries 2 to be cast together with a plastic material in the container 4, 5 in gas-tight manner. The containers 4 can be closed on one side through caps 8 with screw thread 7 or caps 8 lockable by means of snap-in means, whereby the metal or metal alloy 10 to be used as reducing agent is situated on the inside of the screw cap 8 and/or closure cap 8. It is feasible just as well to combine two containers 4, 5 of bundles of capillaries 2, whereby both containers 4, 5 are coupled to each other at one end each in gas-tight manner, whereby the metal and/or metal alloy 10 is arranged at the transition between the two bundles of capillaries 2. The scope of the invention can also provide that the inside of the capillary-shaped hollow spaces 2 is coated with metal or metal alloys. Accordingly, the chemical reaction producing hydrogen as the propellant for expelling the aqueous solution does not necessarily have to proceed just in the internal space 14 or the internal spaces 14, but can also proceed right in the capillaries 2.

FIGS. 3 to 5 present a second variant of an embodiment of the present invention in exemplary manner. FIG. 3 shows a schematic cross-sectional view of another device according to the invention that comprises a hollow body 20 having a cylindrical hollow space. Multiple openings 22 are arranged in the walls of the hollow body 20 at one end of the hollow body 20 and connect the hollow space of the hollow body 20 to the surroundings of the hollow body 20. A perforated rubber sleeve 24 is arranged in front of the inside of the openings 20 and prevents uncontrolled outflow of a fluid medium out of the hollow space.

An overflow channel 26 is arranged in the internal wall of the hollow body 20. A plunger 28 is arranged in the hollow space of the hollow body 20 at the level of the overflow channel 26 and closes tightly against the internal walls of the hollow space of the hollow body 20 by means of an O-ring seal 30, and thus sub-divides the hollow space of the hollow body 20 into a first part (on the left in FIG. 3) and a second part (on the right in FIG. 3). The two parts of the hollow space of the hollow body 20 are connected to each other by means of the overflow channel 26 in the starting position of the plunger 28 shown in the figure.

The hollow body 20 is open on the side opposite to the openings 22 by means of a closure opening having an internal thread. A screw cap 32 is arranged in the closure opening and comprises an external thread by means of which the screw cap 32 can be screwed into the closure opening of the hollow body 20. A seal 33 is arranged at the front end of the screw cap 32 and seals the screw cap 32 and the closure opening and thus the second part of the hollow space of the hollow body 20 with respect to the outside, when the screw cap 32 is screwed into the closure opening.

A pestle 34 is arranged on the front face of the screw cap 32 and is used to press the plunger 28 into the interior of the hollow space of the hollow body 20, when the screw cap 32 is being screwed fully into the hollow body 20. As a result, the plunger 28 is pushed more deeply into the interior of the hollow space such that the overflow channel 26 is then fully arranged in the second part of the hollow space and thus no longer connects the two hollow spaces to each other.

A sponge 36 is arranged about the pestle 34 and a small metal plate 38 made of magnesium and/or iron or an alloy made from these or including these is arranged below it.

FIG. 4 shows a schematic cross-sectional view of a medical implant according to the invention with a similar design as the device according to FIG. 3. The medical implant according to FIG. 4 differs from the device according to FIG. 3 in that an additional opening 22 is arranged at the front face (on the left in FIG. 4) at the front end of the medical implant and/or of the hollow body 20 of the medical implant and is also sealed by means of the perforated rubber sleeve 24. The medical implant comprises a plate 40 at the end of the hollow body 20 that is opposite to the openings 22.

A cross-recessed slit is arranged in the screw cap 32 of the medical implant shown in FIG. 4 and can be used to screw the screw cap 32 into the hollow space using a Phillips-tip screwdriver. Except for these differences, the medical implant according to FIG. 4 has the same design as the device according to FIG. 3. The medical implant can, for example, be a pin, a screw or a bolt that is inserted into a bone, an implant or a spacer for stabilisation purposes.

FIG. 5 shows a schematic cross-sectional view of a spacer according to the invention of a design analogous to the device according to FIG. 3 and/or the medical implant according to FIG. 4. The spacer and its hollow body 20 replicate a femur (upper thigh bone) that ends in a femoral head 44. The purpose of the spacer is to be inserted into a body cavity as a replacement of the final prosthesis to fight an infection at that site.

The embodiments according to FIGS. 3, 4, and 5 all work according to the same functional principle. Initially, the plunger 28 is in the starting position shown. The closure cap 32 is not inserted and therefore the closure opening (on the right in FIGS. 3 to 5) is open. An aqueous solution containing a suitable active substance combination that has been mixed by the physician to suit the application on hand is filled into the hollow space of the hollow body 20 and flows through the overflow channel 26 into the front (first) part of the hollow space as well. Subsequently, the screw cap 32 is screwed into the closure opening. This pushes the plunger 28 more deeply into the interior of the hollow space, past the overflow channel 26, and the hollow space is thus sub-divided into two parts.

The device according to FIG. 3, the medical implant according to FIG. 4 and/or the spacer according to FIG. 5 are then ready for use and can be inserted into the body of a patient in the scope of a surgical intervention. The water of the aqueous solution, which is also present in the second part of the hollow space, reacts with the metal of the small metal plate 38. As a result, hydrogen is produced. The purpose of the sponge 36 is to ensure that the small metal plate 38 gets wetted with the aqueous active substance solution. For this purpose, the sponge 36 soaks up the aqueous solution until it is full.

The hydrogen gas expands in the second part of the hollow space (on the right in FIGS. 3 to 5) and thus drives the plunger 28 towards the openings 22. This causes the aqueous solution in the second part of the hollow space between the openings 22 and the plunger 28 (on the left in FIGS. 3 to 5) to be pressed through the perforated rubber sleeve 24 and the openings 22 out of the device, medical implant and/or spacer. This releases a fluid active substance in the body of the patient both continuously and evenly.

The water in the aqueous active substance solution or the solution of the pharmaceutically active substance undergoes a chemical reaction with the magnesium and/or iron at the metal surface of the small metal plate 38, whereby the metal or metals corrode, which produces metal oxides and gaseous hydrogen. The hydrogen gas produced has a significantly larger volume at standard conditions such that it expands in the second part of the hollow space and thus drives the plunger 28 towards the openings 22 and thus presses-out the aqueous solution from the first part of the hollow space through the perforated rubber sleeve 24 and the openings 22. The chemical reaction of corrosion of the small metal plate 38 proceeds sufficiently slowly in this context such that the aqueous solution is pressed out of the openings 22 only slowly and the device, medical implant and/or spacer therefore releases the active substances evenly over a long period of time. The duration and rate of hydrogen evolution and thus of the active substance release of the device can be adjusted through appropriate selection of the reducing agent, i.e. the selection of the metals of the alloy and the surface properties thereof.

Instead of providing just one small metal plate 38, the internal wall of the second hollow space, the side of the plunger 28 facing the second part of the hollow space and/or the entire front face of the screw cap 32 can consist of or be coated with a metal or a metal alloy having a negative standard potential.

Preferably, the plunger 28 contains an overpressure valve (not shown) such that a connection to the first part of the hollow space is produced by means of the plunger 28 when an excessive overpressure is present in the second part of the hollow space.

In an alternative embodiment of the invention, the overflow channel 26 may be left out. The two parts of the hollow space are then always separated from each other. For this purpose, a fluid active substance is introduced into the first part of the hollow space. Subsequently, the plunger 28 is inserted. Then water, or theoretically any other gas-producing propellant, can be filled into the second part of the hollow space. Then the second part of the hollow space is closed as well. It is feasible to dispense with the pestle 34 in this embodiment. Even though this design and/or its use is somewhat more complex, it is advantageous in that different substances can be contained in the two parts of the hollow space that are specifically tailor-made for the application on hand (effect of the active substances on the one hand and gas production on the other) and thus are particularly well-suited.

The features of the invention disclosed in the preceding description and in the claims, figures, and exemplary embodiments, can be essential for the implementation of the various embodiments of the invention both alone and in any combination.

LIST OF REFERENCE NUMBERS

1 Base body
2 Capillary
4, 5 Housing
6 External thread
7 Internal thread
8 Cap
10 Metal plate
12 Elastic connection
14 Internal space
20 Hollow body
22 Opening
24 Perforated rubber sleeve
26 Overflow channel
28 Plunger
30, 33 O-ring/seal
32 Screw cap/closure
34 Pestle
36 Sponge
38 Small magnesium/iron plate
34 Plate
42 Cross-recessed slit
44 Head of a femoral spacer

The invention claimed is:

1. A method for releasing a fluid active substance from a hollow space of a medical implant, in which a gas is produced through a chemical reaction of liquid water and a reducing agent and the resulting gas pressure is used to expel the fluid active substance out of at least one opening of the hollow space, wherein the hollow space, at least over regions, is formed by a plurality of tubes, wherein a first end of the plurality of tubes is located adjacent to the at least one opening of the hollow space.

2. The method according to claim 1, wherein hydrogen is produced as the gas.

3. The method according to claim 2, wherein a metallic surface is used as the reducing agent, the metallic surface has a negative standard potential, wherein magnesium, iron or alloys comprising magnesium and/or iron is used as the metallic surface, whereby the hydrogen is produced through corrosion of the metallic surface.

4. The method according to claim 3, wherein magnesium and a noble metal is used as the reducing agent and the gas is produced through an electrochemical reaction.

5. The method according to claim 3, wherein a mixture of a quickly corroding metal and a slowly corroding metal is used as the reducing agent.

6. The method according to claim 1, wherein the liquid water used for the chemical reaction is part of an aqueous solution that forms the fluid active substance, wherein the aqueous solution comprises at least one antibiotic.

7. The method according to claim 1, wherein the plurality of tubes are parallel and capillary-shaped tubes.

8. The method according to claim 7, wherein the capillary-shaped tubes are capillaries having a diameter of less than 500 μm.

9. The method according to claim 1, further comprising:
arranging the reducing agent on a second end of the plurality of tubes that is located opposite to the first end of the plurality of tubes.

10. The method according to claim 1, further comprising:
coating a second end of the plurality of tubes with the reducing agent, wherein the second end of the plurality of tubes is located opposite with respect to the first end of the plurality of tubes.

11. The method according to claim 1, wherein the medical implant is a hip spacer or a knee spacer.

12. A method for releasing a fluid active substance from a hollow space of a medical implant, in which a gas is produced through a chemical reaction of liquid water and a reducing agent and the resulting gas pressure is used to expel the fluid active substance out of at least one opening of the hollow space, wherein the length of the hollow space is divided into a first part comprising the at least one opening and a second part that is closed or is closable, wherein the fluid active substance is arranged in the first part and the liquid water and reducing agent is arranged in the second part such that the resulting gas pressure is generated in the closed second part of the hollow space and presses the fluid active substance out of the first part of the hollow space through the at least one opening.

13. The method according to claim 12, wherein a plunger separates the first and second parts of the hollow space from each other in a gas-tight manner.

14. The method according to claim 13, wherein a closure pushes the plunger towards the at least one opening when the closure is being screwed into a closure opening of the medical implant.

15. The method according to claim 13, further comprising:
controlling propulsion of the plunger within the hollow space via a closure, a closure cap or a screw cap.

16. The method according to claim 12, further comprising:
closing the at least one opening by means of a perforated body.

17. The method according to claim 12, further comprising:
arranging a perforated rubber body in the region of the at least one opening.

18. A method for releasing a fluid active substance from a hollow space of a medical implant, in which a gas is produced through a chemical reaction of liquid water and a reducing agent and the resulting gas pressure is used to expel the fluid active substance out of at least one opening of the hollow space, wherein the active substance is continuously released by means of an active transport mechanism; wherein the active transport mechanism is activated at body temperature without requiring an external energy source or an internal energy source for activation.

19. The method according to claim 18, wherein the active substance is continuously released over a period of weeks by the active transport mechanism.

* * * * *